US006281401B1

(12) United States Patent
Randolph

(10) Patent No.: US 6,281,401 B1
(45) Date of Patent: Aug. 28, 2001

(54) OLIGOMERIZATION OF OLEFINS

(75) Inventor: Bruce B. Randolph, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/397,571

(22) Filed: Sep. 16, 1999

(51) Int. Cl.$^7$ ................ C07C 2/16; C07C 2/26
(52) U.S. Cl. ............ 585/515; 585/510; 585/511; 585/526; 585/520; 585/521
(58) Field of Search ................ 585/515, 510, 585/511, 502, 526, 520, 521; 502/155

(56) References Cited

U.S. PATENT DOCUMENTS

| 4,400,565 | 8/1983 | Darden et al. | 585/10 |
| 4,613,723 | * 9/1986 | Olah | 585/730 |
| 4,740,652 | 4/1988 | Frame | 585/512 |
| 5,094,995 | 3/1992 | Butt et al. | 502/402 |
| 5,639,931 | 6/1997 | Hellring et al. | 585/722 |

FOREIGN PATENT DOCUMENTS 59-21629 * 2/1984 (JP) .

OTHER PUBLICATIONS

Chemical Engineers' Handbook; Perry 1973.*

* cited by examiner

Primary Examiner—Marian C. Knode
Assistant Examiner—Thuan D Dang
(74) Attorney, Agent, or Firm—Jeffrey R. Anderson

(57) ABSTRACT

A process for oligomerizing at least one heavy olefin having at least 5 carbon atoms per molecule in the presence of at least one co-fed light olefin having less than 5 carbon atoms per molecule is disclosed. The presence of the at least one co-fed light olefin results in increased $C_6$=($C_6$ olefin) conversion (if present as one of the at least one heavy olefins), increased weight % of $C_{11}$+ hydrocarbons in the $C_9$+ material of the product and increased cetane of the $C_9$+ material of the product as compared to the oligomerization of the at least one heavy olefin without the co-fed at least one light olefin.

20 Claims, No Drawings

OLIGOMERIZATION OF OLEFINS

BACKGROUND OF THE INVENTION

The present invention relates to the field of hydrocarbon upgrading processes. In another aspect, the invention relates to the oligomerization of olefins.

It is known in the art to oligomerize olefins in the presence of an acidic catalyst to diesel fuel range hydrocarbons. As gasoline fuel specifications become more stringent concerning sulfur content, aromatic content and Reid vapor pressure ("RVP"; defined as the vapor pressure of a hydrocarbon at 100° F. (37.8° C.) in pounds per square inch absolute and measured using ASTM test method D-323), the demand for diesel fuel could significantly increase. Therefore, development of a process for oligomerizing olefins to diesel fuel range hydrocarbons wherein the quality of the diesel fuel produced is enhanced, would be a significant contribution to the art and to the economy.

SUMMARY OF THE INVENTION

It is an object of the present invention to provide a process for oligomerizing olefins to diesel fuel range hydrocarbons.

It is yet another object of the present invention to provide a process for oligomerizing olefins wherein the weight % of $C_{11}+$ hydrocarbons contained in the oligomers having at least 9 carbon atoms per molecule in the reactor effluent is enhanced.

It is still another object of the present invention to provide a process for oligomerizing olefins wherein the cetane number of the oligomers having at least 9 carbon atoms per molecule in the reactor effluent is enhanced.

In accordance with the present invention, a method has been found for oligomerizing olefins comprising the steps of:

(a) introducing a heavy hydrocarbon stream comprising at least one heavy olefin having at least 5 carbon atoms per molecule into a reaction zone containing an oligomerization catalyst and operating under reaction conditions for oligomerizing olefins;

(b) introducing a light olefin stream comprising at least one light olefin having less than 5 carbon atoms per molecule at a rate of introduction into the reaction zone as a co-feed with the heavy hydrocarbon stream;

(c) withdrawing from the reaction zone a reactor effluent comprising oligomers having at least 9 carbon atoms per molecule;

(d) identifying a baseline weight % of $C_{11}+$ hydrocarbons contained in the oligomers, based on the total weight of the oligomers, when there is no step (b); and (e) controlling the rate of introduction of the light olefin stream in step (b) such that the weight % of $C_{11}+$ hydrocarbons contained in the oligomers, based on the total weight of the oligomers, of the reactor effluent of step (c) exceeds the baseline weight % of $C_{11}+$ hydrocarbons contained in the oligomers identified in step (d).

Other objects and advantages will become apparent from the detailed description and the appended claims.

DETAILED DESCRIPTION OF THE INVENTION

The catalyst useful in the present invention can be any oligomerization catalyst suitable for oligomerizing olefins to diesel fuel range hydrocarbons. Preferably, the oligomerization catalyst is an acid catalyst. More preferably, the oligomerization catalyst comprises an acid catalyst selected from the group consisting of perfluoropolyalkyl sulfonic acid, perfluoroalkyl sulfonic acid, polyfluoroalkyl sulfonic acid and compounds defined by the formulas:

$C_nX_yF_{(2n+1-y)}SO_3H$;

$C_nX_yF_{(2n-y)}(SO_3H)_2$ and combinations of any two or more thereof, wherein:

X is selected from the group consisting of hydrogen, chlorine, bromine, iodine and combinations of any two or more thereof;

n ranges from 1 to and including 20;

y ranges from 0 to and including 39; and the alkyl groups of the perfluoropolyalkyl sulfonic acid, perfluoroalkyl sulfonic acid and polyfluoroalkyl sulfonic acid can contain in the range of from 1 to 8 carbon atoms.

The presently most preferred oligomerization catalyst comprises an acid catalyst selected from the group consisting of perfluorooctane sulfonic acid, perfluoropolyalkyl sulfonic acid and combinations thereof.

The process of this invention involves a method for oligomerizing olefins. A heavy hydrocarbon stream comprising, consisting essentially of, or consisting of at least one heavy olefin having at least 5 carbon atoms per molecule is introduced or charged to a reaction zone containing an oligomerization catalyst operated under reaction conditions for oligomerizing olefins.

Preferably, the heavy hydrocarbon stream comprises at least one heavy olefin having in the range of from 5 to 6 carbon atoms per molecule. In addition, the heavy hydrocarbon stream can be obtained by fractionation of a gasoline stream, including, but not limited to, fluidized catalytic cracker gasoline, to at least partially remove the $C_5/C_6$ olefin material for use as the heavy hydrocarbon stream in the present invention. This provides the benefits of reduced olefin content in the gasoline stream, reduced RVP of the gasoline stream (due to the removal of the high RVP $C_5$ olefins) and increased diesel fuel production from the $C_5/C_6$ olefin material, which are all expected to be the future regulatory trend.

It has been discovered that the introduction of a light olefin stream as a co-feed, comprising at least one light olefin having less than 5 carbon atoms per molecule, to the reaction zone along with the heavy hydrocarbon stream unexpectedly results in an increased weight % of $C_{11}+$ hydrocarbons in the produced oligomers having at least 9 carbon atoms per molecule as compared to the weight % of $C_{11}+$ hydrocarbons in the produced oligomers having at least 9 carbon atoms per molecule when the light olefin stream is not co-fed. The light olefin stream is preferably a hydrocarbon compound selected from the group consisting of propylene, butylene, isobutylene and combinations of any two or more thereof.

The reactor effluent from the inventive process comprises oligomers having at least 9 carbon atoms per molecule. A baseline weight % of $C_{11}+$ hydrocarbons in the oligomers having at least 9 carbon atoms per molecule ("oligomers") of the reactor effluent is identified representing the baseline weight % of $C_{11}+$ hydrocarbons contained in the oligomers of the reactor effluent when there is no introduction of the light olefin stream co-feed. The identified baseline weight % of $C_{11}+$ hydrocarbons contained in the oligomers of the reactor effluent is generally less than about 40 weight %; more particularly less than about 35 weight %; and most particularly less than 30 weight %, based on the total weight of the oligomers.

The light olefin stream co-feed can be controllably introduced to the reaction zone resulting in a mole ratio of the light olefin stream co-feed to the heavy hydrocarbon stream. The mole ratio of the light olefin stream co-feed to the heavy hydrocarbon stream can be any ratio that can enhance the weight % of $C_{11}+$ hydrocarbons contained in the oligomers of the reactor effluent over the identified baseline weight % of $C_{11}+$ hydrocarbons contained in the oligomers of the reactor effluent when there is no introduction of the light olefin stream co-feed. The weight % of $C_{11}+$ hydrocarbons contained in the oligomers of the reactor effluent when there is a controlled introduction of the light olefin stream co-feed is preferably greater than about 40 weight %; more preferably greater than about 50 weight %; and most preferably greater than 60 weight %. The mole ratio of the light olefin stream co-feed to the heavy hydrocarbon stream can be in the range of from about 0.01:1 to about 4:1; preferably from about 0.5:1 to about 3:1; and most preferably from 1:1 to 2:1.

This increase in weight % of $C_{11}+$ hydrocarbons contained in the oligomers results in an increased cetane number for the $C_9+$ material following hydrogenation, as demonstrated in the Examples.

The oligomerization reaction can take place in any reactor system known to those skilled in the art to be suitable for use in oligomerizing an olefin in the presence of an oligomerization catalyst. Typical reactor systems useful in the present invention include, but are not limited to, batch type operations, a fixed bed system, a moving bed system, and a fluidized bed system.

Any of these operational modes has advantages and disadvantages, and those skilled in the art can select the one most suitable for a particular feed and catalyst system.

The oligomerization reaction is preferably carried out within an oligomerization zone, wherein is contained an oligomerization catalyst system in accordance with the present invention, and under reaction conditions that suitably promote oligomerization of at least a portion of the heavy olefins of the heavy hydrocarbon stream and the light olefins of the co-fed light olefin stream. Optionally, the oligomerization can take place in the presence of hydrogen. The reaction temperature of the oligomerization zone is more particularly in the range of from about 100° F. (37.8° C.) to about 500° F. (260° C.), preferably in the range of from about 150° F. (65.6° C.) to about 300° F. (148.9° C.), and most preferably in the range of from 200° F. (93.3° C.) to 260° F. (126.7° C.). The oligomerization zone is operated at a pressure sufficient to maintain the reactants in liquid form. The contacting pressure of the oligomerization zone is generally within the range of from about 0 psig to about 1000 psig, preferably in the range of from about 50 psig to about 500 psig, and most preferably from 100 psig to 250 psig.

The flow rate at which the combination of the heavy hydrocarbon stream and light olefin stream ("combination") is charged to the oligomerization zone is such as to provide a weight hourly space velocity ("WHSV") in the range of from about 0.01 to about 1000 hour$^{-1}$. The term "weight hourly space velocity", as used herein, shall mean the numerical ratio of the rate at which the combination is charged to the oligomerization zone in pounds per hour divided by the pounds of catalyst contained in the oligomerization zone to which the combination is charged. The preferred WHSV of the combination to the oligomerization zone is preferably in the range of from about 0.25 hour$^{-1}$ to about 250 hour$^{-1}$ and, most preferably, in the range of from 0.5 hour$^{-1}$ to 100 hour$^{-1}$.

The reactor effluent can be separated in a separation unit to produce an overhead stream comprising $C_8-$ components, primarily comprising non-oligomerized $C_5$ olefins and some light olefins (such as propylene and butylenes), and a bottoms stream comprising $C_9+$ components, primarily comprising $C_9+$ olefins. The bottoms stream can then be hydrotreated, in any suitable manner, to produce a good quality (high cetane number) diesel-range stream useful as a diesel blend stock.

The overhead stream can be alkylated, in any suitable alkylation unit, wherein the production of isopentane will be reduced.

The following examples are presented to further illustrate the invention and are not to be construed as unduly limiting its scope.

EXAMPLE I

This example illustrates the preparation of catalysts which were subsequently used as catalysts in the inventive oligomerization process of the present invention.

Catalyst A

A 91.8 gram quantity of silica (Davison G57 grade) was suspended in 500 mL of distilled water. A 31.7 gram quantity of perfluorooctane sulfonic acid salt ($C_8F_{17}SO_3-K^+$) was dissolved in 100 mL of distilled water and added to the silica/water suspension. The mixture was mechanically stirred for 1 hour, then acidified by addition of 40 mL of 98% $H_2SO_4$. Stirring continued for 1 hour and then the solids were settled. The water was decanted and the remaining solids were washed with 100 mL of distilled water and filtered. After filtration, the solid was dried for 24 hours under vacuum. Immediately prior to use, the catalyst was dried at about 80° C. for 4 hours under vacuum. The final catalyst contained 24.4 weight % perfluorooctane sulfonic acid based on the total weight of the catalyst.

Catalyst B

Catalyst B is a catalyst obtained from E. I. DuPont de Nemours and Company under product designation Nation® (catalyst containing 13 weight percent perfluorinated polyalkyl sulfonic acid resin on silica.

EXAMPLE II

This example illustrates the benefits of increased weight % of $C_{11}+$ hydrocarbons contained in the oligomers having at least 9 carbon atoms per molecule of the reactor effluent and increased cetane number for the oligomers having at least 9 carbon atoms per molecule that result from introducing a light olefin stream co-feed in a process of contacting a heavy hydrocarbon stream comprising heavy olefins with Catalyst A or Catalyst B of Example I.

In Run 1 (control), 9.55 grams (22.7 mL volume) of Catalyst A from Example 1 were placed in a stainless steel tube reactor (length: about 18 inches; inner diameter: about 0.5 inch). The steel reactor tube was heated to a temperature of about 257° F. The reactor pressure was about 100 psig. A feed stream comprising $C_5$ olefins and no $C_4-$ olefins was introduced to the reactor tube at a flow rate of 29.4 mL/hour (19.1 grams/hour) to yield a liquid hourly space velocity of 1.3 hr.$^{-1}$ (WHSV of 2.0 hr.$^{-1}$). The term "liquid hourly space velocity", as used herein, shall mean the numerical ratio of the rate at which a feed stream is charged to the reactor tube in mL per hour divided by the volume in mL of catalyst contained in the reactor tube to which the feedstream is charged. The product was analyzed by means of a gas chromatograph. Test data results obtained after 7.5 hours on stream are summarized in Table 1.

In Run 2 (inventive), the reactor contents from Run 1 were utilized. The steel reactor tube was heated to a temperature of about 258° F. The reactor pressure was about 100 psig. A feed stream comprising $C_4$ and $C_5$ olefins was introduced to the reactor tube at a flow rate of 29.4 mL/hour to yield a LHSV of 1.3 (WHSV of about 1.9 hr.$^{-1}$). The product was analyzed by means of a gas chromatograph. Test data results obtained after 7.0 hours on stream are summarized in Table 1.

In Run 3 (control), 17.0 grams of Catalyst B from Example 1 were placed in an autoclave reactor including a stirring shaft and impeller. Air present in the autoclave reactor was evacuated and $N_2$ gas was added to a pressure of 250 psig. At this time, 30 grams of hydrocarbon feed was introduced to the autoclave reactor with a stirring rate of 1000 rpm. The autoclave reactor pressure was maintained at 250 psig and the reactor temperature, after 30 minutes of contact time, was at about 243° F. The product was collected for analysis after 30.0 minutes of contact time and analysis was by means of a gas chromatograph. Test data results are summarized in Table 2.

The remaining product from Control Run 3 was hydrogenated and separated into a $C_9+$ material (diesel range material) and a $C_8-$ material. The cetane of the $C_9+$ material was determined as follows.

A mixture was prepared comprising:

6.8 volume % $C_9+$ material; and 93.2 volume % diesel fuel having a cetane number of 39.5.

The cetane of the mixture was determined using ASTM test method D613.65 and was 40.2. The cetane of the $C_9+$ material was calculated as follows:

$$\left(\frac{6.8 \text{ vol. } \% C_9 + material}{100}\right) * X + \left(\frac{93.2 \text{ vol. } \% \text{ diesel fuel}}{100}\right) * 39.5 = 40.2$$

X=calculated cetane of the $C_9+$ material=49.8.

In Run 4 (inventive), 16.6 grams of Catalyst B from Example 1 were placed in an autoclave reactor including a stirring shaft and impeller. Air present in the autoclave reactor was evacuated and $N_2$ gas was added to a pressure of 250 psig. At this time, 30 grams of hydrocarbon feed was introduced to the autoclave reactor with a stirring rate of 1000 rpm. The autoclave reactor pressure was maintained at 250 psig and the reactor temperature, after 30 minutes of contact time, was at about 257° F. The product was collected for analysis after 30.0 minutes of contact time and analysis was by means of a gas chromatograph. Test data results are summarized in Table 2.

The remaining product from Inventive Run 4 was hydrogenated and separated into a $C_9+$ material (diesel range material) and a $C_8-$ material. The cetane of the $C_9+$ material was determined as follows.

A mixture was prepared comprising:

3.8 volume % $C_9+$ material; and 96.2 volume % diesel fuel having a cetane number of 39.5.

The cetane of the mixture was determined using ASTM test method D613.65 and was 41.7. The cetane of the $C_9+$ material was calculated as follows:

$$\left(\frac{3.8 \text{ vol. } \% C_9 + material}{100}\right) * X + \left(\frac{96.2 \text{ vol. } \% \text{ diesel fuel}}{100}\right) * 39.5 = 41.7$$

X=calculated cetane of the $C_9+$ material=97.4.

TABLE 1

| Component | Control Run 1 | | Inventive Run 2 | |
| --- | --- | --- | --- | --- |
| | Feed Stream wt. % | Product wt. % | Feed Stream wt. % | Product wt. % |
| $C_3$ | — | — | 0.19 | 0.15 |
| $iC_4$ | — | 0.15 | 27.07 | 25.68 |
| $iC_{4-}$ | — | 0.01 | 28.02 | 0.04 |
| $n - C_4$ | 0.01 | 0.01 | 0.58 | 0.60 |
| $2 - C_{4-}$ | — | 0.01 | 0.01 | 0.03 |
| $i - C_5$ | 57.07 | 64.03 | 21.85 | 23.33 |
| $n - C_5$ | 0.02 | 0.06 | 0.01 | 0.02 |
| $1 C_{5-}$ | 14.54 | 0.32 | 10.95 | 0.19 |
| $2 C_{5-}$ | — | 5.28 | — | 3.77 |
| $i C_{5-}$ | 28.29 | 0.35 | 11.01 | 0.21 |
| $C_6 - c_8$* | 0.07 | 1.57 | 0.02 | 2.90 |
| $C_9$ | — | 1.81 | — | 4.22 |
| $C_{10}+$ | — | 26.40 | 0.29 | 38.86 |
| Total | 100 | 100 | 100 | 100 |
| $C_9+$ Product breakdown: (wt % on $C_6+$ basis) | | | | |
| $C_9$ | | 6.1 | | 9.2 |
| $C_{10}$ | | 59.9 | | 21.5 |
| $C_{11}+$ | | 28.7 | | 63.0 |

*The $C_6$–$C_8$ component contains paraffins, olefins, naphthenes and aromatics.

TABLE 2

| Component | Control Run 3 | | Inventive Run 4 | |
| --- | --- | --- | --- | --- |
| | Feed wt. % | Product wt. % | Feed wt. % | Product wt. % |
| $C_3 =$ | | | 3.26 | 0.96 |
| $C_3$ | — | — | 0.34 | 0.37 |
| $iC_4$ | — | 0.10 | 48.20 | 57.63 |
| $iC_4 =$ | — | 0.02 | 0.03 | 0.33 |
| $n - C_4$ | 0.02 | 0.01 | 1.10 | 1.37 |
| $2 - C_4 =$ | 0.13 | 0.04 | 13.03 | 4.79 |
| $i - C_5$ | 19.00 | 21.12 | 6.23 | 7.80 |
| $n - C_5$ | 3.03 | 3.51 | 1.00 | 1.17 |
| $1 C_5 =$ | 1.88 | 0.35 | 0.61 | 0.11 |
| $2 C_5 =$ | 8.43 | 5.11 | 2.78 | 1.28 |
| $i C_5 =$ | 12.87 | 1.06 | 4.32 | 0.38 |
| $C_6 - $'s | 12.08 | 4.60 | 4.10 | 0.86 |
| $C_6 - C_8$* | 42.48 | 44.68 | 14.67 | 13.98 |
| $C_9$ | — | 0.47 | — | 1.23 |
| $C_{10} +$ | 0.08 | 18.93 | 0.33 | 7.74 |
| Total | 100 | 100 | 100 | 100 |
| cetane** | — | 49.8 | — | 97.4 |
| $C_6 =$ conv., wt. % | | 61.9 | | 78.8 |

*The $C_6 - C_8$ component contains paraffins, olefins, naphthenes and aromatics and is substantially depleted of $C_6 = $'s.
**Calculated cetane of the $C_9 +$ material in the product determined using ASTM test method D613.65.

The test data presented in Table 1 show that the addition of $C_4$ olefins to a $C_5$ olefin containing stream in an oligomerization process results in an increased weight % of $C_{11}+$ hydrocarbons in the $C_9+$ material (that is, the oligomers having greater than 9 carbon atoms per molecule) of the product as compared to the weight % of $C_{11}+$ hydrocarbons in the $C_9+$ material of the product from the oligomerization of $C_5$ olefins without added $C_4$ olefins.

Inventive Run 2 demonstrated a 143% increase in the weight % of $C_{11}+$ hydrocarbons in the $C_9+$ material of the product over Control Run 1.

The test data presented in Table 2 show that the addition of $C_3/C_4$ olefins to a $C_5/C_6$ olefin containing stream results in increased $C_6$ olefin conversion and increased cetane for the $C_9+$ material separated from the $C_6+$ material of the product as compared to the $C_6$ olefin conversion and cetane for the $C_9+$ material of the product from the oligomerization of $C_5/C_6$ olefins without added $C_3/C_4$ olefins.

Inventive Run 4 demonstrated a 27.3% increase in $C_6$ olefin conversion and a 95.6% increase in cetane of the $C_9+$ material of the product over Control Run 3. The increase in cetane is believed to be due to a higher weight % of $C_{11}+$ hydrocarbons in the $C_9+$ material of the product from inventive Run 4 over the weight % of $C_{11}+$ hydrocarbons in the $C_9+$ material of the product from Control Run 3.

From the data in Tables 1 and 2, it is readily apparent that the inventive process results in the oligomerization of olefins to diesel fuel range hydrocarbons and that the weight % of $C_{11}+$ hydrocarbons contained in the oligomers having at least 9 carbon atoms per molecule in the reactor effluent and the cetane number of the oligomers are enhanced as compared to the weight % of $C_{11}+$ hydrocarbons and the cetane number of the oligomers when a light olefin having less than 5 carbon atoms per molecule is not controllably introduced to the oligomerization reactor.

Reasonable variations, modifications, and adaptations can be made within the scope of the disclosure and the appended claims without departing from the scope of this invention.

That which is claimed is:

1. A method for oligomerizing heavy olefins comprising:
   (a) introducing a heavy hydrocarbon stream comprising at least one heavy olefin having in the range of from 5 to 6 carbon atoms per molecule into a reaction zone containing an oligomerization catalyst and operating under reaction conditions for oligomerizing heavy olefins;
   (b) introducing a light olefin stream comprising at least one light olefin having less than 5 carbon atoms per molecule at a rate of introduction into said reaction zone as a co-feed with said heavy hydrocarbon stream;
   (c) withdrawing from said reaction zone a reactor effluent comprising oligomers having at least 9 carbon atoms per molecule; and
   (d) wherein the rate of introduction of said light olefin stream in step (b) is sufficient such that the weight % of $C_{11}+$ hydrocarbons contained in the oligomers having at least 9 carbon atoms per molecule, based on the total weight of the oligomers, of said reactor effluent of step (c) exceeds the weight % of $C_{11}+$ hydrocarbons contained in the oligomers having at least 9 carbon atoms per molecule, based on the total weight of the oligomers, of a reaction product produced by a method identical to the method of step (a) without the introduction of the light olefin stream, including the reaction conditions of step (a).

2. A method in accordance with claim 1 wherein said at least one light olefin of said light olefin stream is further characterized to include a hydrocarbon compound selected from the group consisting of propylene, butylene, isobutylene and combinations of any two or more thereof.

3. A method in accordance with claim 1 wherein step (e) additionally provides for a mole ratio of said at least one light olefin to said at least one heavy olefin introduced into said reaction zone in the range of from about 0.01:1 to about 4:1.

4. A method in accordance with claim 1 wherein step (e) additionally provides for a mole ratio of said at least one light olefin to said at least one heavy olefin introduced into said reaction zone in the range of from about 0.05:1 to about 3:1.

5. A method in accordance with claim 1 wherein step (e) additionally provides for a mole ratio of said at least one light olefin to said at least one heavy olefin introduced into said reaction zone in the range of from 1:1 to 2:1.

6. A method in accordance with claim 1 wherein said oligomerization catalyst is an acid catalyst.

7. A method in accordance with claim 1 wherein said oligomerization catalyst is an acid catalyst selected from the group consisting of compounds defined by the formulas:

$C_nX_yF_{(2n+1-y)}SO_3H$;

$C_nX_yF_{(2n-y)}(SO_3H)_2$ 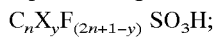 and combinations of any two or more compounds thereof, wherein:

X is selected from the group consisting of hydrogen, chlorine, bromine and iodine;

n is in the range of from 1 to 20; and y is in the range of from 0 to 39.

8. A method in accordance with claim 1 wherein said oligomerization catalyst is perfluorooctanesulfonic acid.

9. A method in accordance with claim 1 wherein said oligomerization catalyst is perfluoropolyalkylsulfonic acid.

10. A method in accordance with claim 1 wherein the reaction conditions of said reaction zone include a reaction temperature in the range of from about 100° F. to about 500° F., a reaction pressure in the range of from about 0 psia to about 500 psia and a weight hourly space velocity in the range of from about 0.01 hr.$^{-1}$ to about 1000 hr.$^{-1}$.

11. A method for oligomerizing heavy olefins comprising:
   (a) introducing a heavy hydrocarbon stream comprising at least one heavy olefin having in the range of from 5 to 6 carbon atoms per molecule into a reaction zone containing an oligomerization catalyst and operating under reaction conditions for oligomerizing heavy olefins;
   (b) introducing a light olefin stream comprising at least one light olefin having less than 5 carbon atoms per molecule at a rate of introduction into said reaction zone as a co-feed with said heavy hydrocarbon stream;
   (c) withdrawing from said reaction zone a reactor effluent comprising oligomers having at least 9 carbon atoms per molecule;
   (d) recovering said oligomers from said reactor effluent; and
   (e) wherein the rate of introduction of said light olefin stream in step (b) is sufficient such that the weight % of $C_{11}+$ hydrocarbons contained in said oligomers, based on the total weight of said oligomers, of said reactor effluent of step (c) exceeds the weight % of $C_{11}+$ hydrocarbons contained in the oligomers of a reaction product produced by a method identical to the method of step (a) without the introduction of the light olefin stream, including the reaction conditions of step (a).

12. A method in accordance with claim 11 wherein said at least one light olefin of said light olefin stream is further characterized to include a hydrocarbon compound selected from the group consisting of propylene, butylene, isobutylene and combinations of any two or more thereof.

13. A method in accordance with claim 11 wherein step (f) additionally provides for a mole ratio of said at least one light olefin to said at least one heavy olefin introduced into said reaction zone in the range of from about 0.01:1 to about 4:1.

14. A method in accordance with claim 11 wherein step (f) additionally provides for a mole ratio of said at least one light olefin to said at least one heavy olefin introduced into said reaction zone in the range of from about 0.5:1 to about 3:1.

15. A method in accordance with claim 11 wherein step (f) additionally provides for a mole ratio of said at least one light olefin to said at least one heavy olefin introduced into said reaction zone in the range of from 1:1 to 2:1.

16. A method in accordance with claim 11 wherein said oligomerization catalyst is an acid catalyst.

17. A method in accordance with claim 11 wherein said oligomerization catalyst is an acid catalyst selected from the group consisting of compounds defined by the formulas:

$C_n X_y F_{(2n+1-y)} SO_3H$;

$C_n X_y F_{(2n-y)} (SO_3H)_2$ and combinations of any two or more compounds thereof, wherein:

X is selected from the group consisting of hydrogen, chlorine, bromine and iodine;

n is in the range of from 1 to 20; and y is in the range of from 0 to 39.

18. A method in accordance with claim 11 wherein said oligomerization catalyst is perfluorooctanesulfonic acid.

19. A method in accordance with claim 11 wherein said oligomerization catalyst is perfluoropolyalkylsulfonic acid.

20. A method in accordance with claim 11 wherein the reaction conditions of said reaction zone include a reaction temperature in the range of from about 100° F. to about 500° F., a reaction pressure in the range of from about 0 psig to about 1000 psig and a weight hourly space velocity in the range of from about 0.01 hr.$^{-1}$ to about 1000 hr.$^{-1}$.

* * * * *